United States Patent [19]

Kuroda et al.

[11] Patent Number: 5,595,747
[45] Date of Patent: Jan. 21, 1997

[54] SLOW-RELEASING COMPOSITIONS CONTAINING HYDROTALCITES WHICH HAVE BEEN INTERCALATED WITH AN ORGANIC ANION AND METHOD OF CONTROLLING INSECTS AND PROTECTING FABRIC FROM INSECTS

[75] Inventors: Kazuyuki Kuroda, Tokyo; Yasuyori Tanaka, Toyonaka; Tadahiro Matsunaga, Kobe, all of Japan

[73] Assignee: Sumitomo Chemical Company, Limited, Osaka, Japan

[21] Appl. No.: 280,462

[22] Filed: Jul. 26, 1994

[30] Foreign Application Priority Data

Jul. 30, 1993 [JP] Japan ............... 5-189899

[51] Int. Cl.$^6$ ............... A01N 25/08
[52] U.S. Cl. ............... 424/405; 424/402; 424/403; 424/409
[58] Field of Search ............... 424/408, 402, 424/403, 405, 409

[56] References Cited

U.S. PATENT DOCUMENTS

| | | | |
|---|---|---|---|
| 4,774,212 | 9/1988 | Drezdon | 502/62 |
| 4,849,006 | 7/1989 | Knudson, Jr. | 71/64.11 |
| 5,256,300 | 10/1993 | Cockett et al. | |
| 5,360,547 | 11/1994 | Cockett et al. | 210/690 |
| 5,380,865 | 1/1995 | Cramp et al. | 548/329.5 |
| 5,391,611 | 2/1995 | Funayama et al. | 524/508 |

FOREIGN PATENT DOCUMENTS

| | | |
|---|---|---|
| 0541358 | 5/1993 | European Pat. Off. |
| 0548940 | 6/1993 | European Pat. Off. |
| 2202575 | 8/1990 | Japan |
| 4259503 | 9/1992 | Japan |

OTHER PUBLICATIONS

Ito et al., *Chemical Abstracts*, vol. 116, 1990, #85962.

Kusakabe et al., *Chemical Abstracts*, vol. 115, 1989, #174640.

*Chemical Abstracts*, vol. 117, No. 11, 1992, Columbus, Ohio, US; abstract No. 106378d, "Cut flower preservative containing silver thiosulfate" & JP-A-04 124 101 (Shintokogyo), 24 Apr. 1992.

*Chemical Abstracts*, vol. 115, No. 18, 1991, Columbus, Ohio, US; abstract No. 185160m, "Fungicidal rubber compositions" & JP-A-03 131 637 (Toshiba Silicone), 28 Jun. 1991.

*Primary Examiner*—Thurman K. Page
*Attorney, Agent, or Firm*—Watson Cole Stevens Davis P.L.L.C.

[57] ABSTRACT

A composition comprising hydrotalcite-like compound intercalated with an organic anion such as organic sulfonic anions, sulfuric acid ester anions, phosphoric acid ester anions, carboxylic anions and N-acylamino acid anions and various active agents such as pesticidal active agents, for example an insecticide, a fungicide, a repellent, etc. and a perfume supported by said hydrotalcite-like compound, can release an active agent gradually over a long time while retaining the active agent stably for a long time, so that it has a long acting effect and can be used for various applications such as a pesticidal formulation.

12 Claims, No Drawings

SLOW-RELEASING COMPOSITIONS CONTAINING HYDROTALCITES WHICH HAVE BEEN INTERCALATED WITH AN ORGANIC ANION AND METHOD OF CONTROLLING INSECTS AND PROTECTING FABRIC FROM INSECTS

The present invention relates to an agent-slow releasing composition. More particularly, it relates to a composition comprising an organic anion-intercalated hydrotalcite-like compound and an agent, and to a method for slowly releasing an agent by using said composition.

Hydrotalcite is a natural mineral found in Ural of Russia and Snarum of Norway. In the past, it was not well studied because these have been found few uses for hydrotalcite, the use as antacids was only major use found for it.

However, it has recently been found that it can be used as additives for plastics and rubbers. Since then the compounds having crystal structure similar to that of hydrotalcite (the so-called hydrotalcite-like compounds or hydrotalcites) have generally been investigated.

The present invention provides the hydrotalcite-like compounds with a new application, that is a use as a carrier or vehicle for slow-releasing compositions of agents.

The present inventors have found that the hydrotalcite-like compounds which have been intercalated with an organic anion or anions can stably retain agents such as pesticides and gradually release the active agents, thereby producing the effects of the active agents for a long period of time.

Thus, the present invention provides a composition comprising a hydrotalcite-like compound intercalated with an organic anion and an active agent supported thereby. It also provide a method for control of pests by releasing an active agent by using said composition.

In the present invention, "the hydrotalcite-like compounds" means hydrotalcite or the compounds having crystal structure similar to that of hydrotalcite, including those hydrotalcites reported in Gypsum & Lime, No. 187 (1983), p. 333–339. In this article, they are described as unfixed-ratio compound represented by the formula (1),

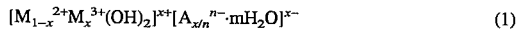

$$[M_{1-x}^{2+}M_x^{3+}(OH)_2]^{x+}[A_{x/n}^{n-}\cdot mH_2O]^{x-} \qquad (1)$$

wherein $M^{2+}$ is a divalent metal cation, $M^{3+}$ is a trivalent metal cation, $A^{n-}$ is an n-valent anion, and x is in the range of $0<x\leq 0.33$.

A metal cation represented by $M^{2+}$ includes magnesium ion, manganese ion, iron ion, cobalt ion, nickel ion, copper ion, zinc ion, etc., a metal cation represented by $M^{3+}$ includes aluminum ion, iron ion, chromium ion, cobalt ion, indium ion, etc., and an anion represented by $A^{n-}$ includes a hydroxyl ion, carbonic ion, fluorine ion, chlorine ion, bromine ion, nitric ion, sulfuric ion, etc.

A preferred organic anion used in the present invention is a relatively bulky anion, and the desirable bulkiness of it is of such a degree that the space between the layers of the hydrotalcite-like compound which is widened by organic anion is enough for molecules of active agent to be included.

Specific examples of the organic anion include organic sulfonic anions, sulfuric acid ester anions, phosphoric acid ester anions, carboxylic anions, N-acylaminoacid anions and the like.

The organic sulfonic anions include, for example, $C_5$–$C_{20}$ alkanesulfonic anions, $C_5$–$C_{20}$ α-olefinsulfonic anions, the sulfonic anions of di($C_5$–$C_{20}$)alkylsulfosuccinic acids, benzenesulfonic anions, naphthalenesulfonic anions, benzenesulfonic anions substituted with a $C_1$–$C_{20}$ alkyl group, naphthalenesulfonic anions substituted with a $C_1$–$C_{20}$ alkyl group, and the like.

The sulfuric acid ester anions include, for example, $C_5$–$C_{20}$ alkylsulfuric acid ester anions, polyoxyethylenealkylethersulfuric acid ester anions in which the mole number of added ethylene oxide molecules is 2 to 10 and the number of carbon atoms of the alkyl group is 3 to 20, polyoxyethylenearylethersulfuric acid ester anions in which the mole number of added ethylene oxide molecules is 2 to 10, $C_6$–$C_{20}$ fatty acid monoglyceridesulfuric acid ester anions, and the like.

The phosphoric acid ester anions include, for example, $C_5$–$C_{20}$ alkylphosphoric acid ester anions, polyoxyethylenealkylether phosphoric acid ester anions in which the mole number of added ethylene oxide molecules is 2 to 20 and the number of carbon atoms of the alkyl group is 3 to 20, polyoxyethylenealkylarylether phosphoric acid ester anions in which the mole number of added ethylene oxide molecules is 2 to 20 and the number of carbon atoms of the alkyl group is 3 to 20, and the like.

The carboxylic anions include, for example, $C_6$–$C_{20}$ fatty acid anions, etc., and the N-acylaminoacid anions include, for example, N-acylsarcosine anions and N-acylalanine anions which are a $C_5$–$C_{20}$ carboxylic acid amide, and the like.

In the present invention, there is no particular limitation to active agents to be supported in the hydrotalcite-like compound intercalated with the organic anion. The active agents include various pesticides (e.g. insecticides, fungicides, repellents, etc.), perfumes and the like.

Specific examples of the insecticides include, pyrethroid compounds such as cyphenothrin, empenthrin, phenothrin, allethrin, prallethrin, permethrin, phthalthrin, cyfluthrin, transfluthrin (benfluthrin), deltamethrin, etofenprox, furamethrin, 2,4-dioxo-1-(2-propynyl) imidazolidin-3-ylmethyl chrysanthemate, etc., organophosphorus compounds such as fenitrothion, etc., insect growth regulating agents such as pyriproxyfen, and fipronil. Specific examples of the repellents include deet.

Examples of the fungicides include 1,2-benzisothiazolin-3-one, 2-n-octyl-4-isothiazolin-3-one, 2-(4-thiazolyl)benzimidazole and 3-iodo-2-propynyl butylcarbamate.

The composition of the present invention can be prepared by homogeneously mixing the active agent, preferably in the form of solutions, with the hydrotalcite-like compound intercalated with an organic anion.

In this process, a solution of the active agent is added in one or several portions or dropwisely to the hydrotalcite-like compound and the resulting mixture is kneaded, and, if necessary, dried. In the case of liquid active agents, they may be added as they are.

Alternatively, the hydrotalcite-like compound intercalated with an organic anion is added to a solution of the active agent and stirred, and then the resulting solid composition is filtrated and dried.

The solvent used in this process may include toluene, xylene, acetone, methanol, ethanol, ethyl acetate, methylene chloride and the like.

In case that the active agent is dissolved in the solvent, the concentrations of the active agents used in this process is preferably in the range of from 5 to 20 wt %.

Further, the composition of the present invention may be prepared by blowing the vapor of the active agent to the hydrotalcite-like compound intercalated with an organic anion and then kneading the resulting mixture.

The amount of the active agent in the slow-releasing composition of the present invention is usually 0.1 to 40 wt %, preferably 1 to 20 wt % of the total weight of the composition.

The hydrotalcite-like compound intercalated with an organic anion can be obtained by removing the inorganic anions (i.e. the anion represented by $A^{n-}$ in the formula (1)) from the layers of the hydrotalcite-like compound by, for example, calcining the hydrotalcite-like compound, and then adding the calcined hydrotalcite-like compound into an aqueous solution containing the organic anion and stirring it.

The calcined hydrotalcite-like compound may be commercially available products such as KYOWAAD® 2000 (an article produced by Kyowa Chemical Industry Co., Ltd.) which has a chemical formula of $Mg_{0.7}Al_{0.3}O_{1.15}$, which is a fine crystal substance comprising MgO and about 30 mol. % $Al_2O_3$ in a solution state on the basis of MgO.

Alternatively, the intercalation of the organic anion into the hydrotalcite-like compound can be carried out by direct exchange of the inorganic anion in the layers with the organic anion. The exchange of the anions can be effected by adding the hydrotalcite-like compound into an aqueous solution containing the organic anion, which is pH of 5 or less, and stirring the mixture at room temperature.

The weight ratio of the organic anion and hydrotalcite-like compound contained in the slow-release composition of the present invention varies with the kind of every component used, but usually it is in the range of 10–75 to 90–25, preferably 50–75 to 50–25 of the organic anion to the hydrotalcite-like compound.

The slow-release composition of the present invention can stably retain the active agent for a long period of time, and can gradually release the active agent over a long period of time, so that it has durability of efficacy of the active agent. Therefore, the slow-release composition of the present invention can be used in agriculture field or public hygiene field.

When the active agent is a pesticidal active agent, thus obtained slow-release composition of the present invention may be further formulated by adding a suitable carrier for pesticidal formulation such as kaolinite, diatomaceous earth, talc, clay, perlite, gypsum, silica and the like. Further, the slow-release composition may be made up into form suitable for uses in agriculture field and public hygiene field, if necessary, by adding auxiliaries such as pH-regulating agents, stabilizers (e.g. light stabilizers) and the like. In this case, the weight proportion of the pesticidal active agent in the whole composition is usually 0.5 to 25%.

The slow-release composition of the present invention can be used as fabric protectants which are particularly required to keep a pest-controlling effect for a long period of time. In this case, pyrethroids having high vapor pressure are useful as the active agent used, and among the pyrethroids, empenthrin and transfluthrin are preferred.

The slow-release composition of the present invention is a powdery form, so that it may be further formulated into any form suitable for the scene of use, for example, packing the composition in a bag made of a highly air-permeable material, interweaving it into pulp, kneading it with a resin, and the like.

The fabric protectant of the present invention can be used to control pest insects or protect fabrics from pest insects by placing it on or in the vicinity of fabric, for example by putting on or hanging in furniture such as wardrobe, drawer and chest.

The method for producing the slow-release composition of the present invention will be illustrated more specifically.

First, general methods A and B will be shown.

Method A

Eight to twenty grams of KYOWAAD® 2000 which has a chemical formula of $Mg_{0.7}Al_{0.3}O_{1.15}$, which is a fine crystal substance comprising MgO and about 30 mol. % $Al_2O_3$ in a solution state on the basis of MgO, is added to 400 g of an aqueous solution containing 5 to 20 wt. % of the sodium salt of the organic anion (prepared with a deionized water). The mixture is stirred at 10° to 30° C. for 1 to 12 hours and then filtered. The solid matter obtained by filtration is vacuum-dried at room temperature for about 24 hours. Thus, the organic anion can be intercalated into the hydrotalcite-like compound. Thereafter, by dropping a predetermined amount of the active agent or solution of the active agent to the resulting solid matter and well kneading the mixture, the composition of the present invention can be obtained.

Method B

The hydrotalcite-like compound intercalated with the organic anion obtained in Method A is added to solution containing 5 to 10 wt. % of active agent, and the mixture is stirred for 1 to 24 hours and filtered. The solid matter obtained by filtration is vacuum-dried at room temperature for about 24 hours to obtain the composition of the present invention.

Production examples for the composition of the present invention will be shown.

PRODUCTION EXAMPLE 1

Sodium dodecylbenzenesulfonate was dissolved in deionized water to obtain 400 g of a 5 wt. % aqueous solution, and 10 g of KYOWAAD®, which has a chemical formula of $Mg_{0.7}Al_{0.3}O_{1.15}$, which is a fine crystal substance comprising MgO and about 30 mol. % $Al_2O_3$ in a solution state on the basis of MgO, was added thereto. The mixture was stirred at room temperature for 1 hour and filtered, and the product obtained by filtration was dried to obtain the hydrotalcite-like compound intercalated with the dodecylbenzenesulfonic anion. One part by weight of cyphenothrin was dropped at 25° C. to 19 parts by weight of this hydrotalcite-like compound obtained, and the mixture was well kneaded to obtain the present composition.

PRODUCTION EXAMPLE 2

Cyphenothrin was dissolved in toluene to obtain a 5 wt. % solution. To 98 parts by weight of this toluene solution was added 2 parts by weight of the hydrotalcite-like compound intercalated with the dodecylbenzene sulfonic anion obtained in Production Example 1, and the mixture was stirred at room temperature for 24 hours. Thereafter, the mixture was filtered, and the product obtained by filtration was dried to obtain the present composition.

PRODUCTION EXAMPLE 3

Procedure was carried out in the same manner as in Production Example 1 except that fenitrothion was used in place of cyphenothrin to obtain the present composition.

PRODUCTION EXAMPLE 4

Procedure was carried out in the same manner as in Production Example 1 except that prallethrin was used in place of cyphenothrin to obtain the present composition.

PRODUCTION EXAMPLE 5

Procedure was carried out in the same manner as in Production Example 1 except that empenthrin was used in place of cyphenothrin to obtain the present composition.

PRODUCTION EXAMPLE 6

Procedure was carried out in the same manner as in Production Example 1 except that 9 parts by weight of the hydrotalcite-like compound intercalated with the dodecylbenzene sulfonic anion was used in place of 19 parts by weight of it, and that empenthrin was used in place of cyphenothrin. Thus, the present composition was obtained.

PRODUCTION EXAMPLE 7

Procedure was carried out in the same manner as in Production Example 6 except that benfluthrin was used in place of empenthrin.

PRODUCTION EXAMPLE 8

Ten parts by weight of the present composition obtained in Production Example 1 and 90 parts by weight of Shokozan Noyaku 50 (clay produced by Shokozan MINING Co., Ltd.) were kneaded together to obtain the present composition.

COMPARATIVE PRODUCTION EXAMPLE 1

Fifty milligrams of empenthrin was dissolved in 2 ml of acetone, and the resulting solution was uniformly dropped to a circular cotton linter having a diameter of 8.5 cm and a thickness of 2 mm. The cotton linter was then air-dried to evaporate acetone. Thus, a comparative composition 1 was obtained.

Test examples of the present compositions will be shown below.

TEST EXAMPLE 1

The content of the active ingredient in the present composition obtained in Production Example 3 was determined by gas chromatography. Thereafter, the composition was put in a polyethylene bag laminated with aluminum, which was then sealed air-tight. After storage at 40° C. for 1 month, the content of the active agent in the composition was determined by gas chromatography. The residual rate of the active ingredient was obtained from the ratio of the contents of the active ingredient to find that it was 89.7%.

TEST EXAMPLE 2

0.225 Gram of the present composition obtained in Production Example 8 was thinly and uniformly scattered on a (15 cm)²-overlaid plywood. A cylindrical plastic (coated with butter on the inner side for preventing cockroaches from running away) having a size of 18 cm in diameter and 5 cm in height was put on the overlaid plywood, and five each of female and male cockroaches were liberated in the cylindrical plastic. After 2 hours, the cockroaches were moved into a cup containing a bait and water, and the mortality of the cockroaches was examined after 3 days. After the test, the overlaid plywood was stored in a dark room, and after 2 and 5 weeks, the same test was carried out. As a result, the mortality was 100% in each case.

TEST EXAMPLE 3

1.0 Gram of each of the compositions obtained in Production Examples 5 and 6 and Comparative Production Example 1 was thinly and uniformly scattered on a Petri dish having a size of 8.5 cm in diameter. Every Petri dish was allowed to stand at room temperature without being covered with a lid. After 1 and 2 months, the content of empenthrin in the composition was quantitatively analyzed to examine the residual rate of empenthrin. The results are shown in Table 1.

TABLE 1

| Test sample | Residual rate (%) After 1 month | After 2 months |
|---|---|---|
| Production Example 5 | 81.5 | 52.8 |
| Production Example 6 | 87.3 | 69.1 |
| Comparative Production Example 1 | 19.8 | 0 |

What is claimed is:

1. A composition comprising an active agent supported on a compound intercalated with organic anions, wherein the compound can be obtained by exchange of inorganic anions $A^{n-}$ of an inorganic compound represented by the formula (1)

$$[M_{1-x}^{2+}M_x^{3+}(OH)_2]^{x+}[A_{x/n}^{n-} \cdot mH_2O]^{x-} \qquad (1)$$

wherein $M^{2+}$ is a divalent metal cation, $M^{3+}$ is a trivalent metal cation, $A^{n-}$ is a n-valent inorganic anion, and x is in the range of $0<x\leq0.33$, with the organic anions.

2. A composition according to claim 1, wherein the active agent is a pesticidal active agent.

3. A composition according to claim 1, wherein the active agent is an insecticidal active agent.

4. A composition according to claim 1, wherein the active agent is one selected from the group consisting of a pyrethroid compound, organophosphorus compound, insect growth controlling agent and repellent.

5. A composition according to claim 1, wherein the active agent is cyphenothrin, empenthrin, phenothrin, allethrin, prallethrin, permethrin, phthalthrin, cyfluthrin, transfluthrin, deltamethrin, etofenprox, furamethrin, 2,4-dioxo-1-(2-propynyl) imidazolidin-3-ylmethyl chrysanthemate, fenitrothion, pyriproxyfen or deet.

6. A composition according to claim 1, wherein the active agent is cyphenothrin, empenthrin or fenitrothion.

7. A composition according to claim 1, wherein the organic anion is organic sulfonic anions, sulfuric acid ester anions, phosphoric acid ester anions, carboxylic anions or N-acylaminoacid anions.

8. A composition according to claim 1, wherein the organic anion is organic sulfonic anions.

9. A composition according to claim 1, wherein the organic anion is dodecylbenzenesulfonic anion.

10. A method of protecting fabric from insects comprising releasing pesticide from a composition comprising a pesticide supported on a compound intercalated with organic anions, wherein the compound can be obtained by exchange of inorganic anions $A^{n-}$ of an inorganic compound represented by the formula (1)

$$[M_{1-x}^{2+}M_x^{3+}(OH)_2]^{x+}[A_{x/n}^{n-} \cdot mH_2O]^{x-} \qquad (1)$$

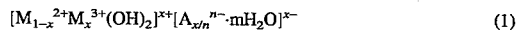

wherein $M^{2+}$ is a divalent metal cation, $M^{3+}$ is a trivalent metal cation, $A^{n-}$ is a n-valent inorganic anion, and x is in the range of 0<x≦0.33, with the organic anions; on or in the vicinity of a fabric.

11. The method according to claim 10, wherein the pesticide is empenthrin or transfluthrin.

12. A method of controlling insects harmful to fabric comprising placing a composition comprising an active agent supported on a compound intercalated with organic anions, wherein the compound can be obtained by exchange of inorganic anions $A^{n-}$ of an inorganic compound represented by the formula (1)

$$[M_{1-x}^{2+}M_x^{3+}(OH)_2]^{x+}[A_{x/n}^{n-} \cdot mH_2O]^{x-} \qquad (1)$$

wherein $M^{2+}$ is a divalent metal cation, $M^{3+}$ is a trivalent metal cation, $A^{n-}$ is a n-valent inorganic anion, and x is in the range of 0<x≦0.33, with the organic anions; on or in the vicinity of the fabric.

* * * * *